(12) United States Patent
Odaka et al.

(10) Patent No.: US 11,001,867 B2
(45) Date of Patent: May 11, 2021

(54) SACCHARIFICATION REACTION MIXTURE, SACCHARIFICATION ENZYME COMPOSITION, SUGAR PRODUCTION METHOD, AND ETHANOL PRODUCTION METHOD

(71) Applicant: NISSAN CHEMICAL CORPORATION, Tokyo (JP)

(72) Inventors: Kazutoshi Odaka, Funabashi (JP); Kazutoshi Sekiguchi, Funabashi (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 247 days.

(21) Appl. No.: 16/307,086

(22) PCT Filed: Jun. 12, 2017

(86) PCT No.: PCT/JP2017/021689
§ 371 (c)(1),
(2) Date: Dec. 4, 2018

(87) PCT Pub. No.: WO2017/217380
PCT Pub. Date: Dec. 21, 2017

(65) Prior Publication Data
US 2019/0300921 A1    Oct. 3, 2019

(30) Foreign Application Priority Data
Jun. 17, 2016 (JP) .............................. JP2016-121206

(51) Int. Cl.
| | |
|---|---|
| *C12P 19/14* | (2006.01) |
| *C12P 7/06* | (2006.01) |
| *C12P 19/02* | (2006.01) |
| *C13K 1/02* | (2006.01) |

(52) U.S. Cl.
CPC ................. *C12P 19/14* (2013.01); *C12P 7/06* (2013.01); *C12P 19/02* (2013.01); *C13K 1/02* (2013.01); *Y02E 50/10* (2013.01)

(58) Field of Classification Search
CPC .. C12P 7/06; C12P 19/02; C12P 19/14; C13K 1/02; Y02E 50/16; Y02E 50/17; Y02E 50/10
See application file for complete search history.

(56) References Cited

U.S. PATENT DOCUMENTS

| | | | | |
|---|---|---|---|---|
| 3,874,991 | A | * | 4/1975 | Kleppe .................. D21C 3/222 162/19 |
| 3,992,261 | A | * | 11/1976 | Takasaki .............. C12N 9/2425 435/95 |
| 4,110,475 | A | | 8/1978 | Singer |
| 4,202,939 | A | | 5/1980 | Mueller et al. |
| 4,209,590 | A | | 6/1980 | MacFadden |

FOREIGN PATENT DOCUMENTS

| | | | |
|---|---|---|---|
| CN | 102776595 A | * | 11/2012 |
| JP | S53-145981 A | | 12/1978 |
| JP | S55-3798 A | | 1/1980 |
| JP | S60-98985 A | | 6/1985 |
| JP | S63-2595 B2 | | 1/1988 |
| JP | S63-21475 B2 | | 5/1988 |
| JP | H10-66594 A | | 3/1998 |
| JP | 2006-136263 A | | 6/2006 |
| JP | 2009-125006 A | | 6/2009 |
| JP | 2011-74522 A | | 4/2011 |
| JP | 2011-234715 A | | 11/2011 |
| JP | 2015-19633 A | | 2/2015 |
| JP | 2016-826 A | | 1/2016 |
| JP | 2016-501937 A | | 1/2016 |
| WO | 2011/078225 A1 | | 6/2011 |
| WO | 2014/085729 A1 | | 6/2014 |
| WO | 2016/021447 A1 | | 2/2016 |

OTHER PUBLICATIONS

Ghosh et al. Enz. Microb. Technol. (1982) 4: 425-430 (Year: 1982).*
Luposi et al. Biotechnol. Bioengineer. (2011) 108(12): 2835-2843 (Year: 2011).*
Machine translation of CN102776595 published 2012 downloaded from the EPO on Sep. 27, 2020 (Year: 2012).*
Sep. 5, 2017 International Search Report issued in International Patent Application No. PCT/JP2017/021689.
Mohsenzadeh et al, "Alkali Pretreatment of Softwood Spruce and Hardwood Birch by NaOH/thiourea, NaOH/urea, NaOH/urea/thiourea, and NaOH/PEG to Improve Ethanol and Biogas Production" Journal of Chemical Technology and Biotechnology, vol. 87, No. 8, 2012, pp. 1209-1214.
Jin et al, "Direct Dissolution of Cellulose in NaOH/thiourea/urea aqueous Solution", Carbohydrate Research, vol. 342, No. 6, Feb. 27, 2007, pp. 851-858.
Mar. 4, 2020 Extended European Search Report issued in European Patent Application No. 17813276.7.

* cited by examiner

*Primary Examiner* — Susan M Hanley
(74) *Attorney, Agent, or Firm* — Oliff PLC

(57) ABSTRACT

A saccharification reaction mixture, a saccharification enzyme composition, and a saccharide production method are aimed to enhance saccharization rate by use of an enzyme in a simple step as well as a method for producing ethanol from a saccharide. The saccharification reaction mixture can saccharify at least one of cellulose and hemicellulose and contains at least one of cellulose and hemicellulose, a saccharification enzyme, silica or a silica-containing substance, and at least one compound (A) selected from the group made of thiourea, a thiourea derivative, an isothiourea derivative, and a salt of any of these.

14 Claims, 3 Drawing Sheets

SACCHARIFICATION REACTION MIXTURE, SACCHARIFICATION ENZYME COMPOSITION, SUGAR PRODUCTION METHOD, AND ETHANOL PRODUCTION METHOD

TECHNICAL FIELD

The present invention relates to a saccharification reaction mixture (or solution or liquid), saccharification enzyme composition, a method for producing a saccharide (or sugar), and a method for producing ethanol.

BACKGROUND ART

Hitherto, there has been known cellulose-origin bioethanol, which is produced from a biomass raw material containing cellulose or hemicellulose.

There has also been known a method for producing a saccharide (e.g., glucose) from a cellulose biomass material containing cellulose or hemicellulose (i.e., a saccharifying technique). In the method, the cellulose biomass material is hydrolyzed with sulfuric acid. The method involves problems such as corrosion of a reactor and treatment of wastewater. In another known saccharifying method, a cellulose biomass material is saccharified in the presence of a solid acid catalyst formed of a carrier (e.g., carbon or zeoilte) on which sulfo groups are present. This method also has problems of a considerably slow reaction rate due to solid reaction and difficulty in separation of the unreacted residue from the solid acid catalyst. Furthermore, in the above methods, difficulty is encountered in controlling hydrolysis. When the hydrolysis reaction proceeds excessively, the formed saccharide decomposes, to thereby lower the yield of the saccharide of interest.

Also, saccharification is known to be performed in the presence of an enzyme (see Patent Document 1). Such a method includes a hydrothermal step of treating a raw material with pressurized hot water, a mechanical crushing step of the hydrothermal treatment product, and a saccharifying step of saccharifying the mechanically crushed product by use of an enzyme. However, according to the method, the rate of saccharifying with an enzyme is low, whereby the produced saccharified liquid docs not always have sufficient concentration, which is problematic.

In order to solve the problem, there has been proposed an improved method which can promote enzymatic reaction more efficiently. In the method, the enzyme is immobilized on a silica meso-porous body in the reaction, whereby the enzyme is caused to be present in the reaction system at a higher concentration, as compared with the case in which the enzyme is dissolved in the reaction system (see Patent Document 2). However, this method involves some problems. Specifically, the method requires an additional step of causing the enzyme to be adsorbed onto the carrier for immobilization, and the thus-immobilized enzyme may attain a reduced reaction efficiency of only about 40 to about 50%, as compared with the case of the same enzyme in a non-immobilized state. Furthermore, difficulty is encountered in separating the unreacted residue from the enzyme-fixed carrier, due to the solid-solid phase reaction.

Also known is a powder-form immobilized enzyme prepared by mixing an enzyme with silica sol, transforming the silica sol to a corresponding silica gel, and crushing the product (see Patent Documents 3 and 4). Even when such a powder-form enzyme is employed, the enzyme can be recovered, but the reaction efficiency is poor. In another known method, vegetable fiber containing cellulose is hydrolyzed with a mixture of an enzyme and a silica powder having a particle size of 0.5 μm to 100 μm. However, the effect of mixing the silica powder cannot be definitely proven, and difficulty is encountered in separating the unreacted residue from the suspended silica powder (see Patent Document 5).

Further, there has been proposed a method for saccharifying a cellulose-origin biomass by use of a saccharification promoter containing an enzyme and a compound such as guanidine or urea (see Patent Document 6). However, the saccharification promoter does not serve as a satisfactory saccharification promoter, but, instead, has such an excellent storage stability that it maintains biomass degradation property even after storage for a specific period of time.

PRIOR ART DOCUMENTS

Patent Documents

Patent Document 1: Japanese Patent Application Laid-Open (kokai) No. 2006-136263
Patent Document 2: Japanese Patent Application Laid-Open (kokai) No. 2009-125006
Patent Document 3: Japanese Patent Publication (kokoku) No. 1988-2595
Patent Document 4: Japanese Patent Publication (kokoku) No. 1988-21475
Patent Document 5: Japanese Patent Application Laid-Open (kokai) No. 1998-66594
Patent Document 6: Japanese Patent Application Laid-Open (kokai) No. 2011-234715

SUMMARY OF THE INVENTION

Problems to be Solved by the Invention

Under such circumstances, the present invention has been accomplished. Thus, objects of the present invention are to provide a saccharification reaction mixture (i.e., a saccharification reaction liquid), a saccharification enzyme composition, and a method for producing a saccharide (or a sugar) (hereinafter may be referred to as a saccharide production method), which are aimed to enhance saccharization rate by use of an enzyme in a simple step. Another object of the present invention is to provide a method for producing ethanol from a saccharide.

Means for Solving the Problems

Accordingly, a first mode of the present invention, in order to attain the above objects, is directed to a saccharification reaction mixture, characterized in that the reaction mixture can saccharify at least one of cellulose and hemicellulose and comprises at least one of cellulose and hemicellulose, a saccharification enzyme, silica or a silica-containing substance, and at least one compound (A) selected from the group consisting of a compound represented by the following formula (1) or (2) and a salt thereof.

[F1]

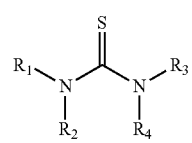

(1)

[F2]

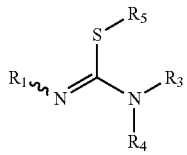

(2)

In formula (1) or (2), $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom.

A second mode of the present invention is a specific embodiment of the saccharification reaction mixture of the first mode, wherein the silica-containing substance is diatomaceous earth or silica sand.

A third mode of the present invention to attain the aforementioned objects is a specific embodiment of the saccharification reaction mixture of the first or second mode, wherein the ratio by mass of compound (A) to silica contained in the silica or silica-containing substance (compound (A)/silica) is 0.00001 to 0.1.

A fourth mode of the present invention to attain the aforementioned objects is a specific embodiment of the saccharification reaction mixture of any of the first to third modes, wherein the compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, S-benzylisothiourea, and S-(2-aminoethyl)isothiourea.

A fifth mode of the present invention, in order to attain the objects, is directed to a saccharification enzyme composition, characterized in that the composition can saccharify at least one of cellulose and hemicellulose and comprises a saccharification enzyme, silica or a silica-containing substance, and at least one compound (A) selected from the group consisting of a compound represented by the following formula (1) or (2) and a salt thereof, wherein the ratio of the mass of silica contained in the silica or silica-containing substance to the mass of compound (A) (compound (A)/silica) is 0.00001 to 0.1.

[F3]

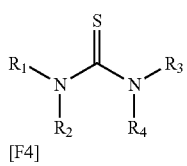

(1)

[F4]

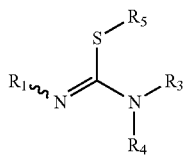

(2)

In formula (1) or (2), $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom.

A sixth mode of the present invention to attain the aforementioned objects is a specific embodiment of the saccharification enzyme composition of the fifth mode, wherein the silica-containing substance is diatomaceous earth or silica sand.

A seventh mode of the present invention to attain the aforementioned objects is a specific embodiment of the saccharification reaction composition of the fifth or sixth mode, wherein the compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, S-benzylisothiourea, and S-(2-aminoethyl)isothiourea.

An eighth mode of the present invention, in order to attain the objects, is directed to a method for producing a saccharide by use of a saccharification reaction mixture which can saccharify at least one of cellulose and hemicellulose, wherein the method comprise employing a saccharification reaction mixture comprising at least one of cellulose and hemicellulose, a saccharification enzyme, silica or a silica-containing substance, and at least one compound (A) selected from the group consisting of a compound represented by the following formula (1) or (2) and a salt thereof.

[F5]

(1)

$$R_1\underset{R_2}{\overset{S}{\underset{|}{N}}}\underset{R_4}{\overset{|}{N}}R_3$$

[F6]

(2)

In formula (1) or (2), $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom.

A ninth mode of the present invention to attain the aforementioned objects is a specific embodiment of the saccharide production method of the eighth mode, wherein the silica-containing substance is diatomaceous earth or silica sand.

A tenth mode of the present invention to attain the aforementioned objects is a specific embodiment of the saccharide production method of the eighth or ninth mode, wherein the ratio of the mass of silica contained in the silica or silica-containing substance to the mass of compound (A) (compound (A)/silica) is 0.00001 to 0.1.

An eleventh mode of the present invention to attain the aforementioned objects is a specific embodiment of the saccharide production method of any of the eighth to tenth modes, wherein the compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, S-benzylisothiourea, and S-(2-aminoethyl)isothiourea.

A twelfth mode of the present invention, in order to attain the objects, is directed to a method for producing ethanol, characterized in that the method comprises subjecting a saccharide produced through a production method of any of the eighth to eleventh modes to ethanol fermentation in the presence of a microorganism which can cause fermentation (hereinafter referred to as "fermentation microorganism"), to thereby produce ethanol.

A thirteenth mode of the present invention to attain the aforementioned objects is a specific embodiment of the ethanol production method of the twelfth mode, wherein the fermentation microorganism is added to a sugar production step, to thereby simultaneously carry out sugar production and ethanol fermentation.

A fourteenth mode of the present invention to attain the aforementioned objects is a specific embodiment of the ethanol production method of the twelfth or thirteenth mode, wherein the fermentation microorganism is a yeast, a mold, or a bacterium.

A fifteenth mode of the present invention to attain the aforementioned objects is a specific embodiment of the ethanol production method of the fourteenth mode, wherein the fermentation microorganism is a microorganism belonging to the genus *Saccharomyces*, a microorganism belonging to the genus *Zymomonas*, a microorganism belonging to the genus *Pichia*, a microorganism belonging to the genus *Candida*, a microorganism belonging to the genus *Zymobacter*, a microorganism belonging to the genus *Corynebacterium*, a microorganism belonging to the genus *Kluyveromyces*, or a microorganism belonging to the genus *Escherichia*.

A sixteenth mode of the present invention to attain the aforementioned objects is a specific embodiment of the ethanol production method of any of the twelfth to fifteenth modes, wherein ethanol fermentation is carried out at 15° C. to 35° C.

Effects of the Invention

The present invention enables provision of a saccharification reaction mixture, a saccharification enzyme composition, and a saccharide production method, which are aimed to enhance saccharification reaction efficiency by use of an enzyme in a simple step, as well as an ethanol production method employing the produced saccharide.

MODES FOR CARRYING OUT THE INVENTION

Figure 1:
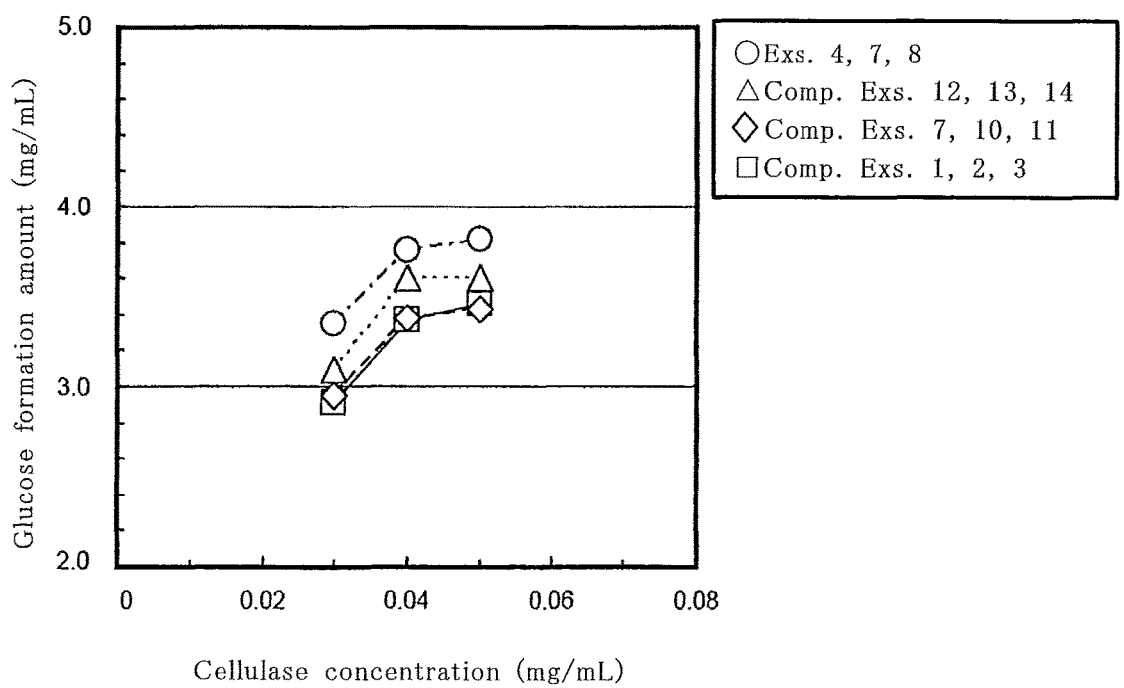
FIG. 1 A graph showing enhancement in saccharification reaction efficiency through addition of thiourea (Examples 4, 7, and 8, and Comparative Examples 1 to 3, 7, and 10 to 14).

In the present invention, at least one of cellulose and hemicellulose is used as a raw material for producing a saccharide such as glucose.

Generally, the cellulose or hemicellulose is contained in cellulose-based biomass materials such as agricultural, forest, and fishery products (e.g., broad-leaved trees and coniferous trees) and wastes thereof. Specific examples include bagasse, rice straw, corn stover, oil palm empty fruit bunches, wood fiber, wood chips, veneer waste chips, sawdust, pulp, waste paper, cotton, sea squirt, and acetic acid bacteria. No particular limitation is imposed on the biomass material, so long as it is derived from a cellulose material. Such biomass materials may be used singly or in combination of two or more species.

Among them, cellulose and hemicellulose derived from sawdust of eucalyptus wood (broad-leaved tree), sawdust of Japanese cedar (coniferous tree), bagasse, rice straw, corn stover, oil palm empty fruit bunches, and cotton are preferred. Although no precise mechanism has been elucidated, these preferred materials are easy to fibrillate, leading to high-yield sugar production.

As used herein, "cellulose" refers to a polymer formed through polymerization of glucose molecules via $\beta$-1,4-glucoside bonds, and "hemicellulose" refers to a water-insoluble polysaccharide other than cellulose, which polysaccharide is a polymer formed through polymerization of glucose, xylose, mannose, galactose, etc. via glucoside bonds.

The cellulose may include cellooligosaccharide or cellobiose, which is a partial decomposition product of cellulose, and may be crystalline or non-crystalline. Also, the cellulose may be a carboxymethylated, aldehydified, or esterified derivative. Notably, as mentioned above, no particular limitation is imposed on the species of cellulose and hemicellulose, so long as they are derived from a biomass material. Thus, the cellulose or hemi cellulose may be derived from plants, fungi, or bacteria.

In the present invention, an enzyme predominantly contains cellulase is used as the saccharification enzyme. The cellulase refers to an enzyme which decomposes cellulose or hemicellulose to a saccharide such as glucose.

No particular limitation is imposed on the microorganism which provides such a saccharification enzyme. Examples of the microorganism include bacteria belonging to the genus *Acremonium*, to the genus *Aspergillus*, to the genus *Chaetomium*, to the genus *Fusarium*, to the genus *Humicola*, to the genus *Irpex*, to the genus *Phanerochaete*, to the genus *Penicillium*, to the genus *Schizophyllum*, to the genus *Sporotrichum*, to the genus *Trametes*, and to the genus *Trichoderma*. Examples of the microorganism also include bacteria belonging to the genus *Clostridium*, to the genus *Pseudomonas*, to the genus *Cellulomonas*, to the genus *Ruminococcus*, and to the genus *Bacillus*, and actinomycetes belonging to the genus *Sulfolobus*, to the genus *Streptomyces*, to the genus *Thermoactinomyces*, and to the genus *Thermomono-*

*spora*. These saccharification enzymes may be artificially modified and may be used singly or in combination of two or more species.

Among them, enzymes derived from bacteria belonging to the genus *Aspergillus* and to the genus *Trichoderma* are preferred, since they have high enzymatic activity on crystalline cellulose.

Alternatively, the cellulase may be a group of enzymes. The enzyme group includes endoglucanase (EC 3.2.1.74), cellobiohydrase (EC 3.2.1.91), β-glucosidase (EC 23.2.4.1, EC 3.2.1.21), etc. Notably, in the present invention, cellulases derived from different bacterial species are preferably used in combination. In this case, saccharization of cellulose or hemicellulose can be more promoted by virtue of the synergistic effect.

The aforementioned cellulase generally has an optimum enzymatic activity at a pH of 3 to 6. However, the cellulase may be an alkaline cellulase, having an optimum enzymatic activity at a pH of 6 to 10. Also, the aforementioned cellulase generally has an optimum enzymatic activity at a reaction temperature of 25° C. to 50° C. However, the cellulase may be a heat-resistant cellulase, having an optimum enzymatic activity at a reaction temperature of 70° C. to 100° C.

In the present invention, silica, diatomaceous earth, or silica sand may be used as the silica or silica-containing substance. The aforementioned diatomaceous earth and silica sand serving as a silica-containing substance are natural products mainly containing silica. Silica collectively refers to compounds containing at least silicon dioxide. Generally, surfaces of silica particles have silanol groups. The silica particles may have a spherical or non-spherical shape. The particles may have a dense (non-hollow) structure or a porous structure, and may be amorphous or crystalline in terms of crystallinity. In use, the particles may be in a form of powder, suspension, or dispersion. The surfaces of silica particles may be partially modified with a functional group other than a silanol group. Alternatively, a compound other than silica may be reacted with a silicon-containing species such as a silane coupling agent, a silicon alkoxide, or silicate ions, to thereby form a silica surface layer. Among these materials, colloidal silica, diatomaceous earth, and silica sand are preferably employed.

In the present invention, the colloidal silica has a mean primary particle size of 1 nm to 400 nm, preferably 5 nm to 350 nm, and is dispersed in the saccharification reaction mixture. The mean primary particle size is calculated by the formula: D (nm)=2720/S, wherein S represents a specific surface area (m$^2$/g) as determined through the nitrogen adsorption method (BET method). In use, the colloidal silica is dispersed in a dispersion medium such as water, methanol, ethanol, acetone, methyl ethyl ketone, or ethylene glycol, to form a dispersion liquid. The dispersion liquid is generally called colloidal liquid, sol, or the like. In the present invention, so long as the enzymatic activity is not inhibited, any dispersion medium may be used. Preferably, the dispersion medium is water, ethanol, or the like.

The colloidal silica may be produced through a water glass method employing water glass as a raw material, an alkoxide method employing a metal alkoxide as a raw material, or a vapor phase method employing a silicon chloride compound as a raw material. Colloidal silica produced through any of these methods may be employed, but colloidal silica produced through the water glass method is preferably employed.

In the present invention, $R_1$ to $R_5$ of any compound represented by formula (1) or (2) each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom. The number of substituents is preferably 1 to 4, more preferably 1 to 3.

[F7]

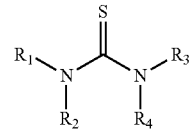

(1)

[F8]

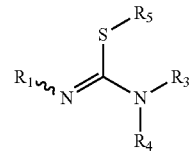

(2)

Specific examples of the aforementioned at least one compound (A) selected from the group consisting of a compound represented by the formula (1) or (2) and a salt thereof include thiourea, a thiourea derivative, and an isothiourea derivative. Examples of the thiourea derivative include N-methylthiourea, 1,3-dimethylthiourea, trimethylthiourea, tetramethylthiourea, 1,3-diethyl-2-thiourea, 1,3-diisoproylthiourea, 1-allyl-2-thiourea, 1-allyl-3-(3-hydroxyethyl)-2-thiourea, 1-acetyl-2-thiourea, (2-methoxyethyl) thiourea, ethylenethiourea, and guanylthiourea. Examples of the isothiourea derivative include S-methylisothiourea, S-ethylisothiourea, S-benzylisothiourea, S-[2-(dimethylamino)ethyl]isothiourea, S-(2-aminoethyl)isothiourea, and S-[4-[(4-nitrobenzyl)oxy]phenethyl]isothiourea. Examples of the salt of the compound represented by formula (1) or (2) include a salt of S-methylisothiourea. Examples of the salt include a hydrochloride, a sulfate, and a hydrobromide. For example, S-(2-aminoethyl)isothiouronium bromide may be used. These compounds may be used singly or in combination or two or more species, in accordance with need. Among them, thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, and S-[2-(dimethylamino)ethyl]isothiourea are preferred, with thiourea, N-methylthiourea, 1,3-dimethylthiourea, trimethylthiourea, tetramethylthiourea, ethylenethiourea, guanylthiourea, S-methylisothiourea, S-ethylisothiourea, and S-[2-(dimethylamino)ethyl]isothiourea being particularly preferred.

The saccharification reaction mixture of the present invention contains at least one of cellulose and hemicellulose as a source, and a saccharification enzyme composition containing a saccharification enzyme, silica or a silica-containing substance, and at least one compound (A) selected from the group consisting of a compound represented by the aforementioned formula (1) or (2) and a salt thereof. From the viewpoint of enjoying the effect of enhancing saccharification reaction efficiency (also referred to simply as reaction efficiency), the saccharification reaction mixture preferably contains silica or a silica-containing substance in combination with compound (A). Details of this will be described in another paragraph.

In the saccharification reaction mixture, the saccharification enzyme concentration is 0.001 mass % to 3.0 mass %, as reduced to BSA (bovine serum albumin) protein concentration, preferably 0.001 mass % to 1.0 mass %. When the saccharification enzyme concentration is lower than 0.001 mass %, reaction efficiency is disadvantageously poor, whereas when the saccharification enzyme concentration is higher than 3.0 mass %, dissolution of the saccharification enzyme is impeded, and cost disadvantageously increases.

In the saccharification reaction mixture, the silica concentration or the silica concentration of the silica-containing substance is 0.001 mass % to 40 mass %, preferably 0.005 mass % to 10 mass %. When the silica concentration or the silica concentration of the silica-containing substance is lower than 0.001 mass %, reaction efficiency is disadvantageously poor, whereas when the colloidal silica concentration is higher than 40 mass %, dispersibility is poor, and cost disadvantageously increases.

In the saccharification reaction mixture, the ratio by mass of the saccharification enzyme to silica (or silica of the silica-containing substance (saccharification enzyme/silica) is 0.0002 to 300, preferably 0.002 to 30. When the (saccharification enzyme/silica) mass ratio falls outside the range, considerable enhancement in reaction efficiency fails to be attained.

In the saccharification reaction mixture, the compound (A) concentration is 0.00001 mass % to 10 mass %, preferably 0.0001 mass % to 1 mass %. When the compound (A) concentration is lower than 0.00001 mass %, reaction efficiency is disadvantageously poor, whereas when the compound (A) concentration is higher than 10 mass %, dispersibility is reduced, and cost disadvantageously increases.

In the saccharification reaction mixture, the ratio by mass of compound (A) to silica (or silica of the silica-containing substance (compound (A)/silica) is 0.00001 to 0.1, preferably 0.0001 to 0.01. When the (compound (A)/silica) mass ratio falls outside the range, considerable enhancement in reaction efficiency fails to be attained.

The pH of the saccharification reaction mixture is 3 to 11, preferably 3 to 6. When the pH is lower than 3, the reaction efficiency of the saccharification enzyme is lowered due to aggregation of silica or a silica-containing substance, whereas when the pH is higher than 11, undesired dissolution of colloidal silica or a silica-containing substance tends to occur. Both cases are not preferred.

Example of the pH-adjusting agent for the saccharification reaction mixture include mineral acids such as sulfuric acid, hydrochloric acid, and nitric acid; carboxylic acids such as acetic acid and oxalic acid; hydroxyacids such as citric acid, tartaric acid, and malic acid; hydroxide salts such as sodium hydroxide and potassium hydroxide; ammonia; and urea. No particular limitation is imposed on the type and concentration of the pH-adjusting agent, so long as the effects of the present invention are not impaired. Also, these pH-adjusting agents may be used singly or in combination of two or more species. Furthermore, the pH-adjusting agent may be used in a buffer having a buffering action.

The reaction temperature of the saccharification reaction mixture of the present invention is preferably 5° C. to 100° C., particularly preferably 20° C. to 55° C. The reaction temperature is preferably adjusted so as to fit to the optimum temperature of the saccharification enzyme. Generally, when the reaction temperature is lower than 5° C., saccharization efficiency considerably decreases, whereas when the reaction temperature is higher than 100° C., the saccharification enzyme may be deactivated. Both cases are not preferred.

Notably, the cellulose biomass material containing cellulose or hemicellulose may be preliminarily treated in a known manner. Generally, the biomass material may be subjected to physical crushing by means of a cutter mill or the like, an acid or alkaline treatment for chemically destructing the structures of lignin, cellulose, and hemicellulose, to thereby provide a raw material to be saccharified.

In preparation of the saccharification reaction mixture, silica or a silica-containing substance and compound (A) may be added to the reaction mixture in which the saccharification enzyme is dispersed. Alternatively, a saccharification enzyme may be added to the reaction mixture in which silica or a silica-containing substance and compound (A) are dispersed. Silica or the silica-containing substance and compound (A) may be added simultaneously or separately. No particular limitation is imposed on the order of addition, so long as the saccharification reaction efficiency does not decrease. Upon addition, compound (A) in the powder or liquid form may be used. Also, so long as the effects of the present invention are not impaired, the pH-adjusting agent and other additives may be added in any order.

As described above, the saccharification reaction mixture of the present invention is produced from at least one of cellulose and hemicellulose as a source, and a saccharification enzyme composition containing a saccharification enzyme, silica, a silica-containing substance, and at least one compound (A) selected from the group consisting of a compound represented by the formula (1) or (2) and a salt thereof. Although no precise mechanism has been elucidated, when silica or the silica-containing substance and compound (A) are used in combination in the saccharification reaction mixture, saccharification of cellulose or hemicellulose can be further promoted.

In addition, since the saccharification reaction mixture of the present invention uses silica or a silica-containing substance in combination with compound (A), the amount of saccharification enzyme can be reduced, which is preferred in terms of cost.

The saccharide produced in the present invention may be subjected to ethanol fermentation in the presence of a microorganism which can cause fermentation, to thereby produce ethanol. Alternatively, after production of a saccharide, the fermentation microorganism which can cause ethanol fermentation may be added, to thereby carry out ethanol fermentation, whereby ethanol is produced. Yet alternatively, the fermentation microorganism which can cause ethanol fermentation may be added to a sugar production step employing the saccharification reaction mixture, to thereby simultaneously carry out sugar production and ethanol fermentation, whereby ethanol is produced.

Examples of the fermentation microorganism of the present invention include a yeast, a mold, and a bacterium. Among them, a yeast or a bacterium are preferred. These fermentation microorganisms may be used singly or in combination of two or more species. Specific examples of the fermentation microorganism include a microorganism belonging to the genus *Saccharomyces*, a microorganism belonging to the genus *Zymomonas*, a microorganism belonging to the genus *Pichia*, a microorganism belonging to the genus *Candida*, a microorganism belonging to the genus *Zymobacter*, a microorganism belonging to the genus *Corynebacterium*, a microorganism belonging to the genus *Kluyveromyces*, or a microorganism belonging to the genus *Escherichia*.

The temperature at which ethanol fermentation is carried out is preferably 15° C. to 35° C., more preferably 28° C. to 32° C. Generally, when the fermentation temperature is lower than 15° C., the fermentation microorganism is less active, thereby considerably reducing the efficiency of ethanol fermentation, whereas when the fermentation temperature is higher than 35° C., the fermentation microorganism may be killed. Both cases are not preferred.

Generally, when ethanol fermentation is carried out by the mediation of a microorganism, a saccharide such as glucose is used as a carbon source for cell proliferation, and a nitrogen source and other nutrients. In the ethanol fermentation of the present invention, the aforementioned saccharide (i.e., glucose) obtained through the saccharification reaction serves as a carbon source. Examples of the nitrogen source include urea, ammonia, and amino acids, and examples of other nutrients include vitamins and minerals. These additives are used in accordance with needs. Notably, in the present invention, urea was used as the nitrogen source in ethanol fermentation.

In ethanol production of the present invention, including ethanol fermentation by use of a fermentation microorganism, silica or a silica-containing substance is employed in combination with compound (A). Therefore, a target saccharide can be produced by a saccharification enzyme at high efficiency, even at a fermentation temperature suitable for ethanol fermentation. Thus, ethanol fermentation of the produced saccharide can also be carried out at high efficiency. Generally, since the reaction temperature for producing saccharide is higher than the fermentation temperature for producing ethanol, the reaction mixture must be cooled before the ethanol fermentation step, resulting in undesired waste in energy. However, according to the effective method of the present invention, the reaction temperature for producing saccharide and the fermentation temperature for producing ethanol may be adjusted to fall within the same range, thereby efficiently avoiding waste of energy.

EXAMPLES

The present invention will next be described in more detail by way of examples, which should not be construed as limiting the invention thereto.

1. Production of Saccharide by Use of Silica as "Silica or Silica-Containing Substance"

1-1. Mean Primary Particle Size

The mean primary particle size of silica particles was measured by means of the following apparatus.

Apparatus in nitrogen adsorption method: Monosorb MS-16 (product of Quantachrome Instruments Japan).

1-2. Cellulase Aqueous Solution

A cellulase aqueous solution was produced through the following procedure. A powder of a cellulase mixture having a specific component ratio was added to deionized water, and the mixture was stirred at room temperature by means of a rotor which was rotated at 100 rpm for 30 minutes, to thereby prepare a cellulase aqueous solution. The cellulase mixture serving as a saccharification enzyme was a mixture (7:3 (w/w)) of a cellulase originating from the genus *Trichoderma reesei* (*T. reesei*) (product of Sigma Aldrich) and a cellulase originating from the genus *Aspergillus niger* (*A. niger*) (product of MP Biomedicals). The cellulase mixture exhibits an optimum enzymatic activity within a pH range of 3 to 6.

1-3. Saccharification Enzyme Aqueous Solutions

Saccharification enzyme aqueous solutions were produced through the following procedure. To deionized water, 1M acetate buffer (for adjusting pH to 5.0) and the aforementioned cellulase aqueous solution were added, so that the buffer concentration was adjusted to 0.05 M. The mixture was stirred at room temperature by means of a rotor which was rotated at 100 rpm for 30 minutes, to thereby prepare saccharification enzyme aqueous solutions having a saccharification enzyme concentration (cellulase concentration in the Examples) shown in Table 1. These saccharification enzyme aqueous solutions were employed as comparative samples 1 to 3. The saccharification enzyme concentration was calculated as a BSA (protein standard substance, product of Sigma Aldrich) protein concentration based on the Bradford method (CBB method). The specific procedure is as follows.

A protein assay CBB solution (5-fold concentrated) (product of Nacalai Tesque) was 5-fold diluted with deionized water. To a disposable cell (cell path length: 10 mm), the diluted CBB solution (2.5 mL) and each comparative sample (0.05 mL) were sequentially added. The disposable cell was tightly closed, and the contents were uniformly mixed in an up and down manner repeatedly. Thereafter, the mixture was allowed to stand for 30 minutes, and the absorbance of the sample was measured at 595 nm by means of a spectrophotometer UV-3150 (product of Shimadzu Corporation). A calibration curve was drawn from absorbance measurements obtained in the same manner from BSA protein concentration-known samples. The saccharification enzyme concentration of the sample was calculated by the thus-drawn calibration curve. Notably, a powder (1 g) of the cellulase derived from the genus *Trichoderma reesei* was found to contain 0.27 g of protein. Also, a powder (1 g) of the cellulase derived from the genus *Aspergillus niger* was found to contain 0.06 g of protein.

TABLE 1

| Saccharification enzyme aq. soln. | Cellulase from | Cellulase concn. mass % | pH |
| --- | --- | --- | --- |
| comp. sample 1 | T. reesei A. niger | 0.003 | 5.0 |
| comp. sample 2 | T. reesei A. niger | 0.004 | 5.0 |
| comp. sample 3 | T. reesei A. niger | 0.005 | 5.0 |

1-4. Saccharification Enzyme Composition

Saccharification enzyme compositions were prepared through the following procedure. To deionized water, 1M acetate buffer (for adjusting pH to 5.0), silica, compound (A), and the aforementioned cellulase aqueous solution were added, so that the buffer concentration was adjusted to 0.05 M. The silica was an acidic silica sol (pH: 2.1, silica concentration: 40 mass %) containing dense spherical colloidal silica (mean primary particle size: 35 nm) produced through the water glass method and dispersed in water, and compound (A) was thiourea. The mixture was stirred at room temperature by means of a rotor which was rotated at 100 rpm for 30 minutes, to thereby prepare saccharification enzyme compositions having a saccharification enzyme concentration (cellulase concentration in the Examples), silica concentration, and compound (A) concentration, shown in Table 2. These saccharification enzyme compositions were employed as samples 1 to 8.

Furthermore, the procedure of preparing samples 1 to 8 was repeated, except that a thiourea derivative or a isothiourea derivative was used as compound (A) instead of thiourea, to thereby prepare different saccharification enzyme compositions. These saccharification enzyme compositions were employed as samples 9 to 18 shown in Table 2. Table 2 shows the saccharification enzyme concentration (i.e., the cellulase concentration in this Example), silica concentration, and compound (A) concentration of each of the samples.

In Table 2, symbols A to K of compound (A) are as follows:
A: thiourea
B: N-methylthiourea
C: 1,3-dimethylthiourea
D: trimethylthiourea
E: tetramethylthiourea
F: 1-allyl-3-(3-hydroxyethyl)-2-thiourea
G: ethylenethiourea
H: guanylthiourea
I: S-methylisothiourea sulfate
J: S-benzylisothiourea hydrochloride
K: S-(2-aminoethyl)isothiouronium bromide hydrobromide saccharification enzyme aqueous solutions were employed as comparative samples 4 to 11.

TABLE 3

| Thiourea-containing saccharification enzyme aqueous soln. | Cellulase from | Cellulase concn. mass % | Thiourea glycol Thiourea concn. mass % | pH |
|---|---|---|---|---|
| comp. sample 4 | T. reesei A. niger | 0.003 | 1 | 5.0 |
| comp. sample 5 | T. reesei A. niger | 0.003 | 0.1 | 5.0 |
| comp. sample 6 | T. reesei A. niger | 0.003 | 0.01 | 5.0 |
| comp. sample 7 | T. reesei A. niger | 0.003 | 0.001 | 5.0 |
| comp. sample 8 | T. reesei A. niger | 0.003 | 0.0001 | 5.0 |
| comp. sample 9 | T. reesei A. niger | 0.003 | 0.00001 | 5.0 |
| comp. sample 10 | T. reesei A. niger | 0.004 | 0.001 | 5.0 |
| comp. sample 11 | T. reesei A. niger | 0.005 | 0.001 | 5.0 |

TABLE 2

| Saccharification enzyme compn. | Cellulase from | Cellulase concn. mass % | Silica Mean primary particle size nm | Silica concn. mass % | compd. (A) Type | compd. (A) concn. mass % | compd. (A)/ silica wt. ratio | pH |
|---|---|---|---|---|---|---|---|---|
| 1 | T. reesei & A. niger | 0.003 | 35 | 1 | A | 1 | 1 | 5.0 |
| 2 | T. reesei & A. niger | 0.003 | 35 | 1 | A | 0.1 | 0.1 | 5.0 |
| 3 | T. reesei & A. niger | 0.003 | 35 | 1 | A | 0.01 | 0.01 | 5.0 |
| 4 | T. reesei & A. niger | 0.003 | 35 | 1 | A | 0.001 | 0.001 | 5.0 |
| 5 | T. reesei & A. niger | 0.003 | 35 | 1 | A | 0.0001 | 0.0001 | 5.0 |
| 6 | T. reesei & A. niger | 0.003 | 35 | 1 | A | 0.00001 | 0.00001 | 5.0 |
| 7 | T. reesei & A. niger | 0.004 | 35 | 1 | A | 0.001 | 0.001 | 5.0 |
| 8 | T. reesei & A. niger | 0.005 | 35 | 1 | A | 0.001 | 0.001 | 5.0 |
| 9 | T. reesei & A. niger | 0.003 | 35 | 1 | B | 0.001 | 0.001 | 5.0 |
| 10 | T. reesei & A. niger | 0.003 | 35 | 1 | C | 0.001 | 0.001 | 5.0 |
| 11 | T. reesei & A. niger | 0.003 | 35 | 1 | D | 0.001 | 0.001 | 5.0 |
| 12 | T. reesei & A. niger | 0.003 | 35 | 1 | E | 0.001 | 0.001 | 5.0 |
| 13 | T. reesei & A. niger | 0.003 | 35 | 1 | F | 0.001 | 0.001 | 5.0 |
| 14 | T. reesei & A. niger | 0.003 | 35 | 1 | G | 0.001 | 0.001 | 5.0 |
| 15 | T. reesei & A. niger | 0.003 | 35 | 1 | H | 0.001 | 0.001 | 5.0 |
| 16 | T. reesei & A. niger | 0.003 | 35 | 1 | I | 0.001 | 0.001 | 5.0 |
| 17 | T. reesei & A. niger | 0.003 | 35 | 1 | J | 0.001 | 0.001 | 5.0 |
| 18 | T. reesei & A. niger | 0.003 | 35 | 1 | K | 0.001 | 0.001 | 5.0 |

1-5. Saccharification Enzyme Aqueous Solution Containing Thiourea

Saccharification enzyme aqueous solutions containing thiourea as compound (A) were prepared through the following procedure. To deionized water, 1M acetate buffer (for adjusting pH to 5.0), thiourea, and the aforementioned cellulase aqueous solution were added, so that the buffer concentration was adjusted to 0.05 M. The mixture was stirred at room temperature by means of a rotor which was rotated at 100 rpm for 30 minutes, to thereby prepare thiourea-containing saccharification enzyme aqueous solutions having a saccharification enzyme concentration (cellulase concentration in the Examples) and thiourea concentration shown in Table 3. These thiourea-containing 1-6. Saccharification Enzyme Aqueous Solution Containing Silica Silica-containing saccharification enzyme aqueous solutions were prepared through the following procedure. To deionized water, 1M acetate buffer (for adjusting pH to 5.0), silica, and the aforementioned cellulase aqueous solution were added, so that the buffer concentration was adjusted to 0.05 M. The silica was an acidic silica sol (pH: 2.1, silica concentration: 40 mass %) containing dense spherical colloidal silica (mean primary particle size: 35 nm) produced through the water glass method and dispersed in water. The mixture was stirred at room temperature by means of a rotor which was rotated at 100 rpm for 30 minutes, to thereby yield silica-containing saccharification enzyme aqueous solutions having a saccharification enzyme concentration (cellulase concentration in the Examples) and silica concentration shown in Table 4. These silica-containing saccharification enzyme aqueous solutions were employed as comparative samples 12 to 14.

TABLE 4

| Silica-containing saccharification enzyme aqueous soln. | Cellulase from | Cellulase concn. mass % | Silica Mean primary particle size nm | Silica concn. mass % | pH |
| --- | --- | --- | --- | --- | --- |
| comp. sample 12 | T. reesei A. niger | 0.003 | 35 | 1 | 5.0 |
| comp. sample 13 | T. reesei A. niger | 0.004 | 35 | 1 | 5.0 |
| comp. sample 14 | T. reesei A. niger | 0.005 | 35 | 1 | 5.0 |

1-7. Saccharification Reaction Mixture

To each of the saccharification enzyme compositions of samples 1 to 18, microcrystalline cellulose powder was added. The powder was dispersed in the composition, to thereby prepare a saccharification reaction mixture employing the corresponding sample. The specific procedure is as follows.

Firstly, each sample (10 mL) was placed in a glass bottle (capacity: 13.5 mL). While the contents were stirred by means of a stirrer (4 mmφ×10 mm), microcrystalline cellulose powder (crystal type: I, Avicel PH-101, product of Sigma Aldrich) was added in an amount of 0.05 g (equivalent to 5 mg/mL). Then, the bottle was tightly closed with a stopper.

Also, the procedure of preparing the saccharification enzyme compositions of samples 1 to 18 was repeated, except that saccharification enzyme aqueous solutions (comparative samples 1 to 3), thiourea-containing saccharification enzyme aqueous solutions (comparative samples 4 to 11), and silica-containing saccharification enzyme aqueous solutions (comparative samples 12 to 14) were used, to thereby yield the corresponding saccharification reaction mixtures of comparative samples.

1-8. Production of Saccharide

A saccharification reaction mixture employing each of the aforementioned samples and comparative samples was caused to be reacted enzymatically in a thermostatic bath (25° C.) under stirring for two days, to thereby form a saccharide (glucose).

1-9. Calculation of Glucose Formation Amount

Example 1

The saccharification reaction mixture obtained from the saccharification enzyme composition of sample 1 (hereinafter, the reaction mixture will be referred to as "saccharification reaction mixture of Example 1") was subjected to the aforementioned enzymatic reaction. Two days after the enzymatic reaction, the amount of formed glucose was calculated through an enzymatic method (GOD method).

A saccharification reaction mixture (sample 1) (0.5 mL) was sampled into a microtube (2 mL), and the enzyme in the tube was deactivated at 105° C. for 15 minutes. Then, the reaction mixture was transferred to a microtube (2 mL) equipped with a filter (absolute pore size: 0.1 μm), so as to remove unreacted cellulose and silica. The mixture was centrifuged means of a high speed refrigerated centrifuge SRX-201 (product of Tomy Seiko Co., Ltd.) at 10,000 G for 5 minutes, and the supernatant was recovered. In the GOD method, Glucose CII-Test Wako (product of Wako Pure Chemical Industries, Ltd.) was used. The absorbance of the sample was measured at 505 nm (cell path length: 10 mm) by means of a spectrophotometer UV-3150 (product of Shimadzu Corporation). The specific procedure is as follows.

To a disposable cell (cell path length: 10 mm), a coloring agent (liquid) (3.0 mL) and the aforementioned supernatant (0.02 mL) were sequentially added. The disposable cell was tightly closed, and the contents were uniformly mixed in an up and down manner repeatedly. Thereafter, the mixture was allowed to stand at 24° C. for 15 minutes, and the absorbance of the sample was measured at 505 nm by means of a spectrophotometer (the absorbance: Es). Separately, to another disposable cell (cell path length: 10 mm), a coloring agent (liquid) (3.0 mL) and 500-mg/dL glucose standard liquid II (0.02 mL) were sequentially added. The disposable cell was tightly closed, and the contents were uniformly mixed in an up and down manner repeatedly. Thereafter, the mixture was allowed to stand at 24° C. for 15 minutes, and the absorbance of the sample was measured at 505 nm by means of a spectrophotometer (the absorbance: Estd). In this measurement procedure, the absorbance of the saccharification reaction mixture of Example 1 (Es) and that of glucose standard liquid II (Estd) were measured with respect to the absorbance of the coloring agent (liquid) 3.0 mL) as a reference sample.

Next, the amount (mg/mL) of formed glucose from the saccharification reaction mixture of Example 1 was determined by the following formula (3). Table 5 shows the results.

MF1

$$\text{Glucose formation amount} = (Es/Estd) \times 5 \quad (3)$$

Examples 2 to 18

In the same manner as employed in Example 1, the saccharification reaction mixtures obtained from the saccharification enzyme compositions of samples 2 to 18 (hereinafter, the reaction mixtures will be referred to as "saccharification reaction mixtures of Examples 2 to 18") were subjected to the enzymatic reaction. Two days after the enzymatic reaction, the amount of formed glucose from each mixture was calculated. Table 5 shows the results.

TABLE 5

| | | Enzym. reaction conditions | | | |
| --- | --- | --- | --- | --- | --- |
| | Saccharification enzyme compn. | Cellulose concn. mg/mL | Reaction temp. ° C. | Reaction time day | Glucose amount mg/mL |
| Ex. 1 (ref.) | sample 1 | 5 | 25 | 2 | 3.11 |
| Ex. 2 | sample 2 | 5 | 25 | 2 | 3.40 |
| Ex. 3 | sample 3 | 5 | 25 | 2 | 3.29 |
| Ex. 4 | sample 4 | 5 | 25 | 2 | 3.35 |
| Ex. 5 | sample 5 | 5 | 25 | 2 | 3.39 |

TABLE 5-continued

| | Saccharification enzyme compn. | Enzym. reaction conditions | | | |
|---|---|---|---|---|---|
| | | Cellulose concn. mg/mL | Reaction temp. ° C. | Reaction time day | Glucose amount mg/mL |
| Ex. 6 | sample 6 | 5 | 25 | 2 | 3.29 |
| Ex. 7 | sample 7 | 5 | 25 | 2 | 3.76 |
| Ex. 8 | sample 8 | 5 | 25 | 2 | 3.82 |
| Ex. 9 | sample 9 | 5 | 25 | 2 | 3.34 |
| Ex. 10 | sample 10 | 5 | 25 | 2 | 3.28 |
| Ex. 11 | sample 11 | 5 | 25 | 2 | 3.48 |
| Ex. 12 | sample 12 | 5 | 25 | 2 | 3.36 |
| Ex. 13 | sample 13 | 5 | 25 | 2 | 3.20 |
| Ex. 14 | sample 14 | 5 | 25 | 2 | 3.31 |
| Ex. 15 | sample 15 | 5 | 25 | 2 | 3.33 |
| Ex. 16 | sample 16 | 5 | 25 | 2 | 3.28 |
| Ex. 17 | sample 17 | 5 | 25 | 2 | 3.26 |
| Ex. 18 | sample 18 | 5 | 25 | 2 | 3.26 |

Comparative Examples 1 to 14

In the same manner as employed in Example 1, the saccharification reaction mixtures obtained from the saccharification enzyme aqueous solution of comparative samples 1 to 3, the thiourea-containing saccharification enzyme aqueous solution of comparative samples 4 to 11, and the silica-containing saccharification enzyme aqueous solution of comparative samples 12 to 14 (hereinafter, the reaction mixtures will be referred to as "saccharification reaction mixtures of Comparative Examples 1 to 14") were subjected to enzymatic reaction (1-8). Two days after the enzymatic reaction, the amount of formed glucose from each mixture was calculated. Table 6 shows the results.

TABLE 6

| | Saccharification enzyme aq. solns. | Enzym. reaction conditions | | | |
|---|---|---|---|---|---|
| | | Cellulose concn. mg/mL | Reaction temp. ° C. | Reaction time day | Glucose amount mg/mL |
| Comp. 1 | comp. sample 1 | 5 | 25 | 2 | 2.91 |
| Comp. 2 | comp. sample 2 | 5 | 25 | 2 | 3.37 |
| Comp. 3 | comp. sample 3 | 5 | 25 | 2 | 3.46 |
| Comp. 4 | comp. sample 4 | 5 | 25 | 2 | 2.67 |
| Comp. 5 | comp. sample 5 | 5 | 25 | 2 | 2.94 |
| Comp. 6 | comp. sample 6 | 5 | 25 | 2 | 2.89 |
| Comp. 7 | comp. sample 7 | 5 | 25 | 2 | 2.95 |
| Comp. 8 | comp. sample 8 | 5 | 25 | 2 | 2.87 |
| Comp. 9 | comp. sample 9 | 5 | 25 | 2 | 2.94 |
| Comp. 10 | comp. sample 10 | 5 | 25 | 2 | 3.38 |
| Comp. 11 | comp. sample 11 | 5 | 25 | 2 | 3.43 |
| Comp. 12 | comp. sample 12 | 5 | 25 | 2 | 3.09 |
| Comp. 13 | comp. sample 13 | 5 | 25 | 2 | 3.60 |
| Comp. 14 | comp. sample 14 | 5 | 25 | 2 | 3.60 |

1-10. Saccharification Reaction Efficiency

Saccharification reaction efficiency of each saccharification reaction mixture was assessed on the basis of the glucose formation amount shown in Table 5 or 6. Firstly, from the glucose formation amounts obtained in Examples 4, 7, and 8, and Comparative Examples 1 to 3, 7, and 10 to 14, the effect of thiourea addition on enhancement in saccharification reaction efficiency was investigated.

FIG. 1 is a graph showing enhancement in saccharification reaction efficiency through addition of thiourea (Examples 4, 7, and 8, and Comparative Examples 1 to 3, 7, and 10 to 14). As shown in FIG. 1, in comparison of saccharification reaction mixtures of Comparative Examples 1 to 3 with those of Comparative Examples 12 to 14, saccharification reaction mixtures of Comparative Examples 12 to 14, prepared by adding silica to the corresponding cellulase aqueous solution, exhibited larger glucose formation amounts, indicating enhancement in saccharification reaction efficiency. In comparison of saccharification reaction mixtures of Comparative Examples 12 to 14 with those of Examples 4, 7, and 8, saccharification reaction mixtures of Examples 4, 7, and 8, prepared by adding silica and thiourea to the corresponding cellulase aqueous solution, exhibited larger glucose formation amounts, indicating further enhancement in saccharification reaction efficiency. In contrast, in comparison of saccharification reaction mixtures of Comparative Examples 1 to 3 with those of Comparative Examples 7, 10, and 11, even when thiourea was added to the corresponding cellulase aqueous solution, no effect of enhancing saccharification reaction efficiency was observed. Therefore, in cellulose saccharification reaction, enhancement in saccharification reaction efficiency was confirmed through combination use of silica and thiourea.

Furthermore, in terms of the amount of cellulase, saccharification reaction mixtures of Comparative Examples 1 to 3 were compared with those of Comparative Examples 12 to 14, prepared by adding silica to the corresponding cellulase aqueous solution. As a result, the amount of cellulase was reduced at about 20%, when any of the saccharification reaction mixtures of Comparative Examples 12 to 14 was used. Also, in terms of the amount of cellulase, saccharification reaction mixtures of Comparative Examples 1 to 3 were compared with those of Examples 4, 7, and 8, prepared by adding silica and thiourea to the corresponding cellulase aqueous solution. As a result, the amount of cellulase can be expected to be reduced at about 30%, when any of the saccharification reaction mixtures of Examples 4, 7, and 8 is used. As compared with the case where silica was added to the corresponding cellulase aqueous solution, the amount of cellulase used in saccharification reaction is thought to be further reduced by about 10%.

Figure 2:
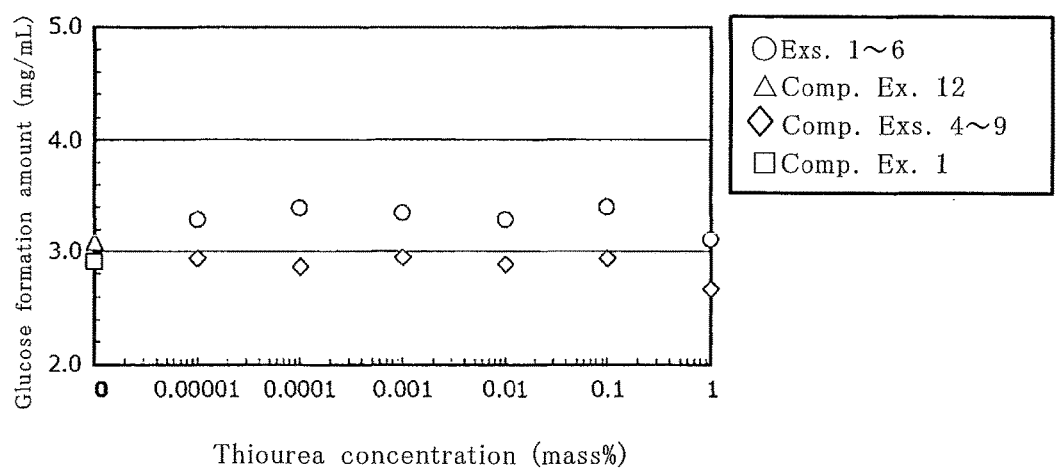
FIG. 2 A graph showing enhancement in saccharification reaction efficiency vs. thiourea concentration (Examples 1 to 6, and Comparative Examples 1, 4 to 9, and 12).

Next, the effect of the amount of thiourea addition (i.e., thiourea concentration) on enhancement in saccharification reaction efficiency was investigated, from the glucose formation amounts obtained in Examples 1 to 6, and Comparative Examples 1, 4 to 9, and 12. FIG. 2 is a graph showing enhancement in saccharification reaction efficiency, with respect to thiourea concentration (Examples 1 and 6, and Comparative Examples 1, 4 to 9, and 12).

As shown in FIG. 2, when the ratio by mass of thiourea to silica (thiourea/silica) was about 0.00001 to about 0.1, saccharification reaction efficiency was remarkably enhanced, confirming the effect of combination use of thiourea and silica. Therefore, the glucose formation amount was suggested to depend particularly on the amount of thiourea added. Note that when only thiourea was added to the saccharification enzyme (cellulase), no effect of enhancing saccharification reaction efficiency was observed.

Figure 3:
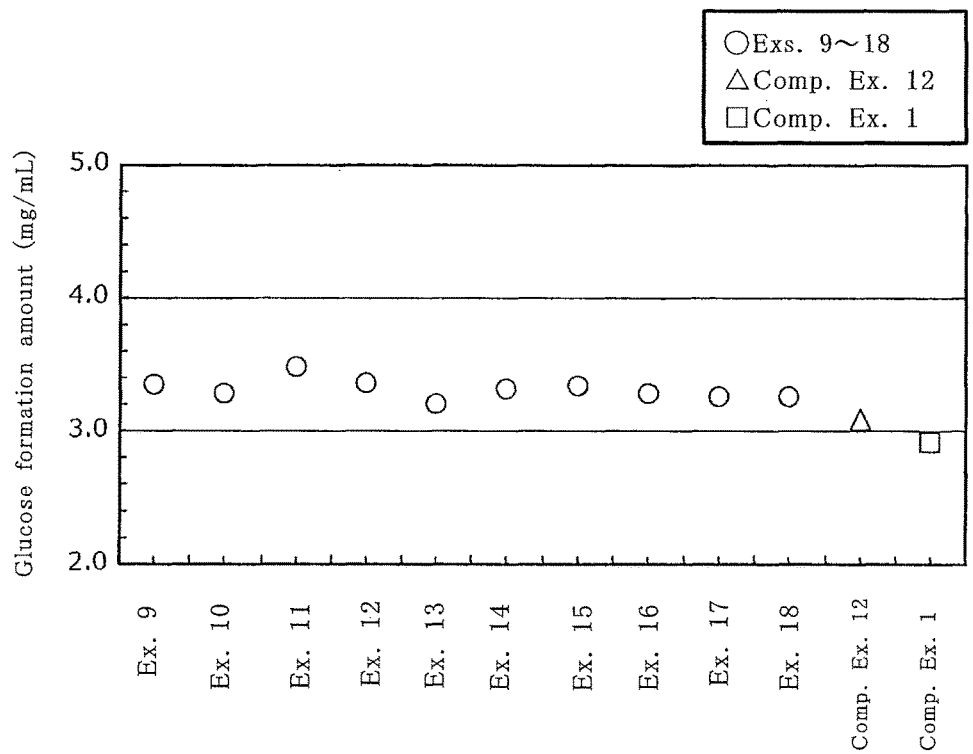
FIG. 3 A graph showing enhancement in saccharification reaction efficiency through addition of a thiourea derivative or an isothiourea derivative (Examples 9 to 18, and Comparative Examples 1 and 12).

Also, from the glucose formation amounts obtained in Examples 9 to 18, and Comparative Examples 1 and 12, the effect of addition of compound (A) other than thiourea (i.e., a thiourea derivative or an isothiourea derivative) on enhancement in saccharification reaction efficiency was investigated. FIG. 3 is a graph showing enhancement in saccharification reaction efficiency through addition of a thiourea derivative or an isothiourea derivative (Examples 9 to 18, and Comparative Examples 1 and 12).

As shown in FIG. 3, in comparison of saccharification reaction mixtures of Examples 9 to 18 with those of Comparative Examples 1 and 12, the effect of enhancement in saccharification reaction efficiency was observed in saccharification reaction mixtures of Examples 9 to 18, prepared by adding silica with a thiourea derivative or an isothiourea derivative, to the corresponding cellulase aqueous solution. As a result, when silica was used with a thiourea derivative or an isothiourea derivative, as compound (A), in cellulose saccharification reaction, enhancement in saccharification reaction efficiency was confirmed.

thereby prepare a saccharification enzyme composition having a saccharification enzyme concentration (cellulase concentration in the Example), a diatomaceous earth concentration, and a thiourea concentration, shown in Table 7. The saccharification enzyme composition was employed as sample 19.

2-3. Saccharification Enzyme Aqueous Solution Containing Diatomaceous Earth

A saccharification enzyme aqueous solution containing diatomaceous earth was produced through the following procedure. To deionized water, 1M acetate buffer (for adjusting pH to 5.0), a silica-containing substance, and the aforementioned cellulase aqueous solution were added, so that the buffer concentration was adjusted to 0.05 M. The silica-containing substance used was diatomaceous earth (Silica #600S, product of Chuo Silika Co., Ltd., silica content: 90 mass %, mean secondary particle size: 30 μm). The mixture was stirred at room temperature by means of a rotor which was rotated at 100 rpm for 30 minutes, to thereby prepare a diatomaceous earth-containing aqueous saccharification enzyme solution having a saccharification enzyme concentration (cellulase concentration in the Example) and a diatomaceous earth concentration, shown in Table 7. The diatomaceous earth-containing saccharification enzyme aqueous solution was employed as comparative sample 15.

TABLE 7

|  |  | Cellulase | | Diatomaceous earth | | Thiourea | | |
| --- | --- | --- | --- | --- | --- | --- | --- | --- |
|  |  | Cellulase from | Cellulase concn. mass % | Mean secondary particle size μm | Diatomaceous earth concn. (silica concn.) mass % | Thiourea concn. mass % | Thiourea/ silica wt. ratio | pH |
| Saccharification enzyme compn. | sample 19 | T. reesei A. niger | 0.003 | 30 | 1 (0.9) | 0.001 | 0.001 | 5.0 |
| Diatomaceous earth-containing saccharification enzyme aq. soln. | comp. sample 15 | T. reesei A. niger | 0.003 | 30 | 1 (0.9) | — | — | 5.0 |

2. Production of Saccharide by Use of Diatomaceous Earth as "Silica or Silica-Containing Substance"

2-1. Mean Secondary Particle Size

The mean secondary particle size of diatomaceous earth particles was measured by means of the following analyzer: Laser diffraction particle size analyzer: LA-300 (product of HORIBA Ltd.)

2-2. Saccharification Enzyme Composition

A saccharification enzyme composition was produced through the following procedure. To deionized water, 1M acetate buffer (for adjusting pH to 5.0), a silica-containing substance, compound (A), and the aforementioned cellulase aqueous solution were added, so that the buffer concentration was adjusted to 0.05 M. The silica-containing substance used was diatomaceous earth (Silica #600S, product of Chuo Silika Co., Ltd., silica content: 90 mass %, mean secondary particle size: 30 μm), and thiourea was used as compound (A). The mixture was stirred at room temperature by means of a rotor which was rotated at 100 rpm for 30 minutes, to 2-4. Saccharification Reaction Mixture The procedure of preparing the saccharification enzyme compositions of samples 1 to 18 was repeated, except that the saccharification enzyme composition of sample 19 and the diatomaceous earth-containing saccharification enzyme aqueous solution of comparative sample 15 were used, to thereby yield the corresponding saccharification reaction mixtures of sample 19 and comparative sample 15.

2-5. Calculation of Glucose Formation Amount

Example 19

In a manner similar to that employed in Example 1, the saccharification reaction mixture obtained from the saccharification enzyme composition of sample 19 (hereinafter, the reaction mixture will be referred to as "saccharification reaction mixture of Example 19") was subjected to enzymatic reaction. Two days after the enzymatic reaction, the amount of formed glucose was calculated. Table 8 shows the results.

Comparative Example 15

In a manner similar to that employed in Example 1, the saccharification reaction mixture obtained from the saccharification enzyme composition of comparative sample 15 (hereinafter, the reaction mixture will be referred to as "saccharification reaction mixture of Comparative Example 15") was subjected to enzymatic reaction. Two days after the enzymatic reaction, the amount of formed glucose was calculated. Table 8 shows the results.

TABLE 8

| | | | Enzym. reaction conditions | | | |
|---|---|---|---|---|---|---|
| | | | Cellulose concn. mg/mL | Reaction temp. °C. | Reaction time day | Glucose amount mg/mL |
| Ex. 19 | Saccharification enzyme composition | sample 19 | 5 | 25 | 2 | 3.29 |
| Comp. Ex. 15 | Diatomaceous earth-containing saccharification enzyme aq. soln. | comp. sample 15 | 5 | 25 | 2 | 2.97 |

2-6. Saccharification Reaction Efficiency

Figure 4:
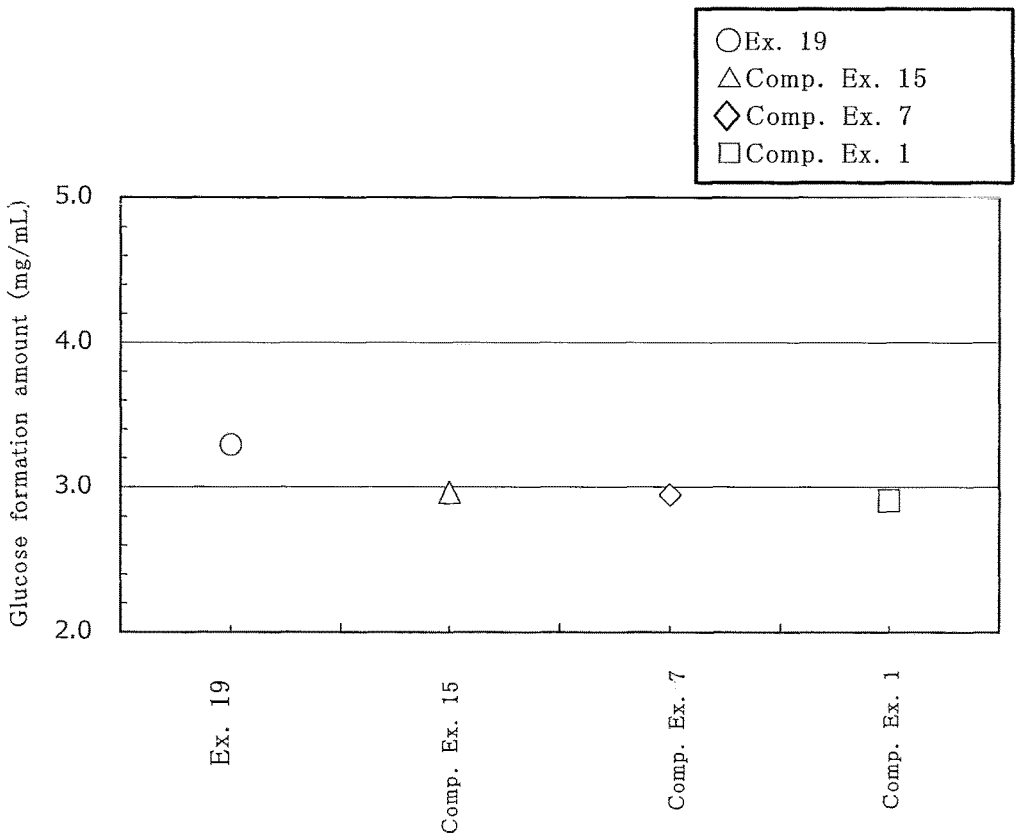
FIG. 4 A graph showing enhancement in saccharification reaction efficiency through addition of thiourea (Example 19 and Comparative Examples 1, 7, and 15).

Saccharification reaction efficiency of each of the samples and comparative samples was assessed on the basis of the glucose formation amounts shown in Tables 6 and 8. Firstly, from the glucose formation amounts obtained in Example 19, and Comparative Examples 1, 7, and 15, the effect of thiourea addition on enhancement in saccharification reaction efficiency was investigated. FIG. 4 is a graph showing enhancement in saccharification reaction efficiency through addition of thiourea (Example 19, and Comparative Examples 1, 7, and 15).

As shown in FIG. 4, among the saccharification reaction mixture of Comparative Example 1; the saccharification reaction mixture of Comparative Example 7, prepared by adding thiourea to the cellulase aqueous solution; the saccharification reaction mixture of Comparative Example 15, prepared by adding diatomaceous earth (i.e., a silica-containing substance) to the cellulase aqueous solution; and the saccharification reaction mixture of Example 19, prepared by adding diatomaceous earth and thiourea to the cellulase aqueous solution, an increase in glucose formation amount was observed in the saccharification reaction mixture of Example 19, prepared by adding diatomaceous earth and thiourea to the cellulase aqueous solution, confirming enhancement in saccharification reaction efficiency. Therefore, when diatomaceous earth was used as a silica-containing substance in combination with thiourea in cellulose saccharification reaction, enhancement in saccharification reaction efficiency was confirmed.

3. Production of Ethanol by Use of Saccharide 3-1. Yeast Aqueous Solution

An yeast aqueous solution was prepared through the following procedure. To deionized water (40 g) preliminarily maintained at 35° C., yeast powder (0.2 g) was added, and the mixture was maintained at 35° C. While the mixture was maintained at 35° C., the contents were dissolved by stirring the mixture by means of a magnetic stirrer for 20 minutes, to thereby yield a 0.5-mass % (i.e., yeast powder (0.2 g)/deionized water (40 g)) yeast aqueous solution. As the yeast, *Saccharomyces cerevisiae* (*S. cerevisiae*) YP2 (product of Sigma Aldrich) belonging to the genus *Saccharomyces* was used.

3-2. Ethanol Fermentation Aqueous Solution

An ethanol fermentation aqueous solution was prepared through the following procedure. To deionized water, sulfuric acid, urea, the aforementioned cellulase aqueous solution, and the aforementioned yeast aqueous solution were added, so that the final pH and the nitrogen source concentration were adjusted to about 5 and 0.21 mg/mL, respectively. The mixture was stirred at room temperature by means of a magnetic stirrer for 10 minutes, to thereby prepare an ethanol fermentation aqueous solution having a saccharification enzyme concentration (cellulase concentration in the Example) and a yeast concentration shown in Table 9. The ethanol fermentation aqueous solution was employed as comparative sample 16.

3-3. Ethanol Fermentation Composition

An ethanol enzyme composition was prepared through the following procedure.

To deionized water, sulfuric acid, urea, the aforementioned cellulase aqueous solution, a silica-containing substance, compound (A), and the aforementioned yeast aqueous solution were added, so that the final pH and the nitrogen source concentration were adjusted to about 5 and 0.21 mg/mL, respectively. The silica-containing substance was an alkaline silica sol (pH: 9.5, silica concentration: 40 mass %) containing dense spherical colloidal silica (mean primary particle size: 85 nm) produced through the water glass method and dispersed in water, and compound (A) was thiourea. The mixture was stirred at room temperature by means of a magnetic stirrer for 10 minutes, to thereby prepare an ethanol fermentation composition having a saccharification enzyme concentration (cellulase concentration in the Examples), a silica concentration, a thiourea concentration, and a yeast concentration shown in Table 9. The ethanol fermentation composition was employed as samples 20 and 21.

3-4. Ethanol Fermentation Aqueous Solution Containing Thiourea

A thiourea-containing ethanol fermentation aqueous solution was prepared through the following procedure. To deionized water, sulfuric acid, urea, thiourea (as compound (A)), the aforementioned cellulase aqueous solution, and the aforementioned yeast aqueous solution were added, so that the final pH and the nitrogen source concentration were adjusted to about 5 and 0.21 mg/mL, respectively. The mixture was stirred at room temperature by means of a magnetic stirrer for 10 minutes, to thereby prepare a thiourea-containing ethanol fermentation aqueous solution having a saccharification enzyme concentration, a thiourea concentration, and a yeast concentration, shown in Table 9. The thiourea containing ethanol fermentation aqueous solution was employed as comparative samples 17 and 18.

3-5. Ethanol Fermentation Aqueous Solution Containing Silica

A silica-containing ethanol fermentation aqueous solution was prepared through the following procedure. To deionized water, sulfuric acid, urea, silica, the aforementioned cellulase aqueous solution, and the aforementioned yeast aqueous solution were added, so that the final pH and the nitrogen source concentration were adjusted to about 5 and 0.21 mg/mL, respectively. The silica was an alkaline silica sol (pH: 9.5, silica concentration: 40 mass %) containing dense spherical colloidal silica (mean primary particle size: 85 nm) produced through the water glass method and dispersed in water. The mixture was stirred at room temperature by means of a rotor which was rotated at 100 rpm for 30 minutes, to thereby prepare a silica-containing ethanol fermentation aqueous solution having a saccharification enzyme concentration (cellulase concentration in the Examples), a silica concentration, and a yeast concentration, shown in Table 9. The silica-containing ethanol fermentation aqueous solution was employed as comparative sample 19.

3-7. Production of Ethanol

A saccharification reaction/ethanol fermentation mixture employing each of the aforementioned samples and comparative samples was caused to be reacted enzymatically in a thermostatic bath (31° C.) under stirring for two days. During reaction, a saccharide (glucose) was formed, and ethanol fermentation was simultaneously performed by use of the formed saccharide, to thereby produce ethanol.

3-8. Calculation of Ethanol Formation Amount

Example 20

The saccharification reaction/ethanol fermentation mixture obtained from the ethanol fermentation composition of

TABLE 9

| | | Cellulase aq. soln. | | Silica sol | | Thiourea | | Yeast aq. soln. | | |
|---|---|---|---|---|---|---|---|---|---|---|
| | | Cellulase from | Cellulase concn. mass % | Mean primary particle size nm | Silica concn. mass % | Thiourea concn. mass % | Thiourea/ silica wt. ratio | Yeast from | Yeast concn. mass % | pH |
| EtOH fermentation compn. | sample 20 | T. reesei A. niger | 0.01 | 85 | 0.5 | 0.05 | 0.1 | S. cerevisiae | 0.05 | 5.4 |
| | sample 21 | T. reesei A. niger | 0.01 | 85 | 0.5 | 0.1 | 0.2 | S. cerevisiae | 0.05 | 5.4 |
| EtOH fermentation aq. solution | comp. sample 16 | T. reesei A. niger | 0.01 | — | — | — | — | S. cerevisiae | 0.05 | 4.9 |
| Thiourea- containing EtOH fermentation aq. solution | comp. sample 17 | T. reesei A. niger | 0.01 | — | — | 0.05 | — | S. cerevisiae | 0.05 | 5.0 |
| | comp. sample 18 | T. reesei A. niger | 0.01 | — | — | 0.1 | — | S. cerevisiae | 0.05 | 5.0 |
| Silica-containing EtOH fermentation aq. solution | comp. sample 19 | T. reesei A. niger | 0.01 | 85 | 0.5 | — | — | S. cerevisiae | 0.05 | 5.3 |

3-6. Saccharification Reaction/Ethanol Fermentation Mixture

To the ethanol fermentation composition of sample 20, microcrystalline cellulose powder was added. The powder was dispersed in the composition, to thereby prepare a saccharification reaction/ethanol fermentation mixture employing the sample. The specific procedure is as follows.

Firstly, each sample (10 mL) was placed in a glass bottle (capacity: 13.5 mL). While the contents were stirred by means of a stirrer (4 mm×4×10 mm), microcrystalline cellulose powder (crystal type: I, Avicel PH-101, product of Sigma Aldrich) was added in an amount of 0.20 g (equivalent to 20 mg/mL). Then, the bottle was closed with a silicone stopper equipped with a hydrophobic PTEF membrane filter (absolute pore size: 0.22 μm).

Also, the procedure of preparing the ethanol fermentation composition of sample 20 was repeated, except that the ethanol fermentation composition (sample 21), an ethanol aqueous fermentation solution (comparative sample 16), thiourea-containing ethanol fermentation aqueous solutions (comparative samples 17 and 18), and a silica-containing substance-containing ethanol fermentation aqueous solution (comparative sample 19) were used, to thereby yield the corresponding saccharification reaction/ethanol fermentation mixtures.

sample 20 (hereinafter, the reaction mixture will be referred to as "saccharification reaction/ethanol fermentation mixture of Example 20") was subjected to enzymatic reaction and ethanol fermentation. After the enzymatic reaction and ethanol fermentation, the amount of formed ethanol was calculated through gas chromatography (GC).

The saccharification reaction/ethanol fermentation mixture of Example 20 (0.5 mL) was sampled into a microtube (2 mL), and the enzyme and yeast in the tube was deactivated at 105° C. for 15 minutes. Then, the reaction mixture was centrifuged by means of a high speed refrigerated centrifuge SRX-201 (product of Tomy Seiko Co., Ltd.) at 15,000 G for 30 minutes, so as to remove unreacted cellulose, the silica-containing substance, and yeast. Thereafter, the supernatant was recovered. Ethanol formation amount was determined by means of a gas chromatograph GC-2014s (product of Shimadzu Corporation) through the one-point calibration method. Table 10 shows the ethanol formation amount measurements (mg/mL). The specific analytical conditions are as follows.

<Analytical Conditions>
Column: Polar Pack Q, length: 1 m, I.D.: 3.2 mm (product of GL Science)
Detector: FID
Column temperature: 150° C.
Flow rate: 40 mL/min
Sample amount: 2 μL
Standard: 10 mg/mL ethanol aqueous solution

Example 21

In the same manner as that of Example 20, the saccharification reaction/ethanol fermentation mixture obtained from the ethanol fermentation composition of sample 21 (hereinafter, the reaction mixture will be referred to as "saccharification reaction/ethanol fermentation mixture of Example 21") was subjected to enzymatic reaction and ethanol fermentation. Two days thereafter, the amount of formed ethanol was calculated. Table 10 shows the results.

Comparative Examples 16 to 19

In the same manner as that of Example 20, each of the saccharification reaction/ethanol fermentation mixtures obtained from an ethanol fermentation aqueous solution (comparative sample 16), thiourea-containing ethanol fermentation aqueous solutions (comparative samples 17 and 18), and a silica-containing substance-containing ethanol fermentation aqueous solution (comparative sample 19) (hereinafter, the reaction mixtures will be referred to as "saccharification reaction/ethanol fermentation mixtures of Comparative Examples 16 to 19") were subjected to saccharification reaction and ethanol fermentation. Two days thereafter, the amount of formed ethanol was calculated. Table 10 shows the results.

TABLE 10

|  |  |  | Enzymatic reaction conditions | | | Formed |
| --- | --- | --- | --- | --- | --- | --- |
|  |  |  | Cellulose concn. mg/mL | Reaction temp. ° C. | Reaction time day | EtOH amount mg/mL |
| Ex. 20 | EtOH fermentation | sample 20 | 20 | 31 | 2 | 3.61 |
| Ex. 21 | compn. | sample 21 | 20 | 31 | 2 | 4.34 |
| Comp. Ex. 16 | EtOH fermentation Aq. soln. | comp. sample 16 | 20 | 31 | 2 | 2.32 |
| Comp. Ex. 17 | Thiourea-containing EtOH | comp. sample 17 | 20 | 31 | 2 | 2.29 |
| Comp. Ex. 18 | fermentation Aq. soln. | comp. sample 18 | 20 | 31 | 2 | 2.49 |
| Comp. Ex. 19 | Silica-containing EtOH fermentation Aq. soln. | comp. sample 19 | 20 | 31 | 2 | 3.31 |

3-9. Ethanol Fermentation Efficiency

Figure 5:
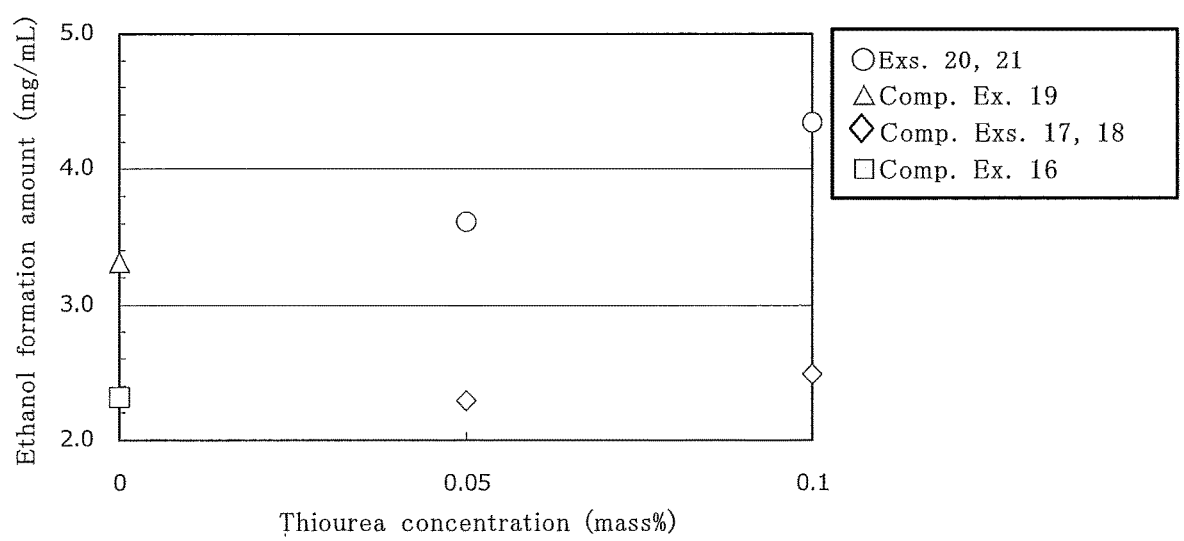
FIG. 5 A graph showing enhancement in ethanol fermentation efficiency vs. thiourea concentration (Examples 20 and 21, and Comparative Examples 16 to 19).

Ethanol fermentation efficiency of each of the saccharification reaction/ethanol fermentation mixtures of the Examples and Comparative Examples was assessed on the basis of the ethanol formation amount shown in Table 10. From the ethanol formation amounts obtained in Examples 20, 21 and Comparative Examples 16 to 19, the effect of the amount of thiourea added (i.e., thiourea concentration) on enhancement in saccharification reaction efficiency was investigated. FIG. 5 is a graph showing enhancement in ethanol fermentation efficiency through addition of thiourea (Examples 20, 21 and Comparative Examples 16 to 19).

As shown in FIG. 5, in comparison of saccharification reaction/ethanol fermentation mixture of Comparative Example 19 with that of Comparative Example 16, the mixture of Comparative Example 19, prepared by adding silica to the aqueous cellulase solution and the yeast aqueous solution, exhibited an increase in ethanol formation amount, indicating enhancement in ethanol formation efficiency. Also, in comparison of saccharification reaction/ethanol fermentation mixtures of Examples 20 and 21, with the mixture of Comparative Example 19, the mixtures of Examples 20 and 21, prepared by adding silica and thiourea to the cellulase aqueous solution and the yeast aqueous solution, exhibited an increase in ethanol formation amount, indicating further enhancement in ethanol formation efficiency. In contrast, in the cases of saccharification reaction/ethanol fermentation mixtures of Comparative Examples 16, 17, and 18, even when thiourea was added to the corresponding cellulase aqueous solution and yeast aqueous solution, no effect of enhancing ethanol formation efficiency was observed. Therefore, in cellulose saccharification reaction and ethanol fermentation, enhancement in ethanol formation efficiency was confirmed through combination use of a silica-containing substance and thiourea.

INDUSTRIAL APPLICABILITY

The present invention can be applied to an industrial field where saccharification technique is employed to form a saccharide such as glucose from a cellulose-origin biomass (including cellulose and hemicellulose). One such application is production of bioethanol from a cellulose material.

The invention claimed is:

1. A saccharification reaction mixture, wherein the reaction mixture can saccharify at least one of cellulose and hemicellulose and comprises:
   at least one of cellulose and hemicellulose,
   a saccharification enzyme,
   silica or a silica-containing substance, and
   at least one compound (A) selected from the group consisting of a compound represented by the following formula (1), a salt thereof, a compound represented by the following formula (2), and a salt thereof:

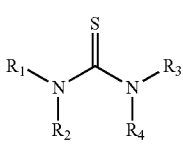

(1)

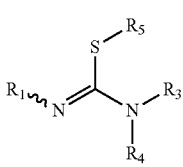

(2)

wherein $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom; and wherein a ratio by mass of the at least one compound (A) to silica present in the silica or the silica-containing substance (compound (A)/silica) is in a range of from 0.00001 to 0.1.

2. The saccharification reaction mixture according to claim 1, wherein the silica-containing substance is diatomaceous earth or silica sand.

3. The saccharification reaction mixture according to claim 1, wherein the at least one compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, and S-(2-aminoethyl)isothiourea.

4. A saccharification enzyme composition, wherein the composition can saccharify at least one of cellulose and hemicellulose and comprises:
a saccharification enzyme,
silica or a silica-containing substance, and
at least one compound (A) selected from the group consisting of a compound represented by the following formula (1), a salt thereof, a compound represented by the following formula (2), and a salt thereof:

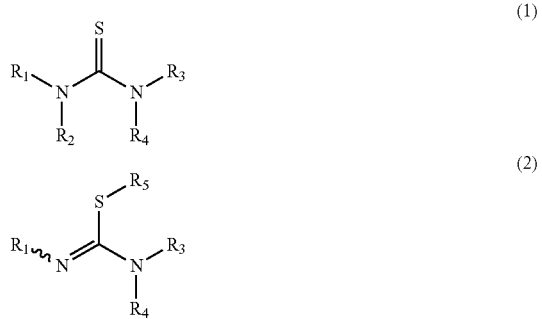

wherein $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom, and wherein a ratio of a mass of silica present in the silica or the silica-containing substance to a mass of the at least one compound (A) (compound (A)/silica) is in a range of from 0.00001 to 0.1.

5. The saccharification enzyme composition according to claim 4, wherein the silica-containing substance is diatomaceous earth or silica sand.

6. The saccharification reaction composition according to claim 4, wherein the at least one compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, and S-(2-aminoethyl)isothiourea.

7. A method for producing a saccharide by use of a saccharification reaction mixture which can saccharify at least one of cellulose and hemicellulose, wherein the method comprise employing a saccharification reaction mixture comprising at least one of cellulose and hemicellulose, a saccharification enzyme, silica or a silica-containing substance, and at least one compound (A) selected from the group consisting of a compound represented by the following formula (1), a salt thereof, a compound represented by the following formula (2), and a salt thereof:

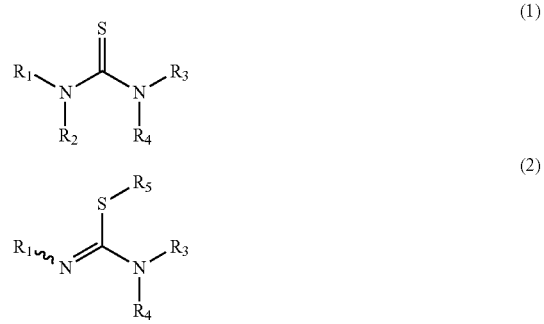

wherein $R_1$ to $R_5$ each represent a hydrogen atom or a C1 to C4 alkyl group, and hydrogen atoms of the alkyl group may be partially substituted by an allyl group, a hydroxyl group, an ester group, an amino group, a carboxyl group, a cyano group, a nitro group, a sulfo group, a phosphono group, or a halogen atom; and wherein a ratio by mass of the at least one compound (A) to silica present in the silica or the silica-containing substance (compound (A)/silica) is in a range of from 0.00001 to 0.1.

8. The saccharide production method according to claim 7, wherein the silica-containing substance is diatomaceous earth or silica sand.

9. The saccharide production method according to claim 7, wherein the at least one compound (A) includes at least one member selected from the group consisting of thiourea, N-methylthiourea, 1,3-dimethylthiourea, trimethylthiourea, tetramethylthiourea, 1-allyl-3-(3-hydroxyethyl)-2-thiourea, ethylenethiourea, guanylthiourea, S-methylisothiourea, S-ethylisothiourea, S-[2-(dimethylamino)ethyl]isothiourea, and S-(2-aminoethyl)isothiourea.

10. A method for producing ethanol, the method comprises: producing a saccharide via the saccharide production method according to claim 7; and subjecting the saccharide to ethanol fermentation in the presence of a fermentation microorganism, to thereby produce ethanol.

11. The method for producing ethanol according to claim 10, wherein the fermentation microorganism is added to a sugar production step, to thereby simultaneously carry out sugar production and ethanol fermentation.

12. The method for producing ethanol according to claim 10, wherein the fermentation microorganism is a yeast, a mold, or a bacterium.

13. The method for producing ethanol according to claim 12, wherein the fermentation microorganism is a microorganism belonging to the genus *Saccharomyces*, a microorganism belonging to the genus *Zymomonas*, a microorganism belonging to the genus *Pichia*, a microorganism belonging to the genus *Candida*, a microorganism belonging to the genus *Zymobacter*, a microorganism belonging to the genus *Corynebacterium*, a microorganism belonging to the genus *Kluyveromyces*, or a microorganism belonging to the genus *Escherichia*.

14. The method for producing ethanol according to claim 10, wherein ethanol fermentation is carried out at 15° C. to 35° C.

* * * * *